United States Patent [19]

Armstrong

[11] Patent Number: 5,354,315
[45] Date of Patent: Oct. 11, 1994

[54] CARDIAC STIMULATOR WITH DATA CONVERTER FOR CARDIAC SIGNAL

[75] Inventor: Randolph K. Armstrong, Missouri City, Tex.

[73] Assignee: Intermedics, Inc., Angleton, Tex.

[21] Appl. No.: 72,471

[22] Filed: Jun. 4, 1993

[51] Int. Cl.⁵ ............................................. A61N 1/362
[52] U.S. Cl. .................................... 607/4; 364/413.06
[58] Field of Search ..................... 607/4, 5, 30, 32; 128/702; 364/413.06; 375/27

[56] References Cited

U.S. PATENT DOCUMENTS

| | | | |
|---|---|---|---|
| 4,557,266 | 12/1985 | Schober | 607/30 |
| 4,625,730 | 12/1986 | Fountain et al. | 607/4 |
| 5,012,411 | 4/1991 | Policastro et al. | 364/413.06 |
| 5,217,021 | 6/1993 | Steinhaus et al. | 128/702 |

OTHER PUBLICATIONS

John Proakis, Digital Communications, second ed., McGraw-Hill Book Co., 1989, pp. 79–86.
Gallager, Robert, Information Theory and Reliable Communication, John Wiley & Sons, 1968, pp. 43–49.

Primary Examiner—George Manuel
Attorney, Agent, or Firm—John R. Merkling

[57] ABSTRACT

An implantable cardiac stimulator with an analog-to-digital converter which comprises timing means for defining measurement cycles. During successive cycles, the value of a cardiac waveform is sampled. The difference between sampled values in two different measurement cycles produces a value whose probability is predicted. A digital code is assigned to each expected difference value such that difference values with a high expected probability have a shorter code and values with a low probability have a longer code. Means are provided for assigning a digital code based on the determined difference, the digital code being of predetermined variable size, the size of the code being proportional to the predicted probability of occurrence of a particular difference. The variability in code length permits the resulting digital representation of the waveform to be compressed and the energy required for conversion to be reduced. Different codes can be assigned to a detected difference depending on the type of waveform (normal, tachycardia, fibrillation) which is being detected.

22 Claims, 4 Drawing Sheets

CARDIAC STIMULATOR WITH DATA CONVERTER FOR CARDIAC SIGNAL

TECHNICAL FIELD

My Invention relates to implantable cardiac stimulators, including pacemakers and implantable defibrillators, which can detect electrical activity in the heart and which have the capacity to store representations of such electrical activity or transmit a representation to an external monitor or both. In particular, my invention relates to a data converter for converting a sensed analog waveform to a compressed digital representation.

BACKGROUND OF MY INVENTION

The heart pumps blood throughout the body in response to natural electrical stimuli which occur in the atrium and ventricle of the heart. If the natural electrical stimuli are disrupted or lost, the heart will not provide the circulation needed to sustain life. Implanted electrical devices which stimulate the heart have been used to correct various conditions. A pacemaker can be used to correct bradycardia, the condition wherein the heart beats too slowly. The heart may also beat too quickly (an arrhythmia or tachycardia) or it may quiver erratically (fibrillation). Electrical devices, including implantable defibrillators, have been designed to respond to such conditions and provide therapeutic electrical stimulation to the heart.

In using these devices, it is frequently desirable for a physician to be able to study the waveforms being produced in the heart, either naturally or in response to stimulation. In general, the implanted device senses the electrical condition of the heart through one or more leads implanted in or near the heart tissue. The sensed phenomenon can be transmitted directly from the implanted device to an external monitor for study by a physician, or the waveforms may be stored in some fashion and transmitted later. In either situation, it has been recognized that storage or transmission of direct analog data is difficult at best, and impractical in many cases. Data is frequently better transmitted in digital form, particularly where the monitor may be remote from the patient as, for example, when the data is to be transmitted by telephone connection to a physician at a different location.

SUMMARY OF MY INVENTION

I have invented an analog-to-digital converter which is particularly adapted for use in an implantable cardiac stimulator. The converter comprises timing means for defining measurement cycles. During successive cycles, the value of a cardiac waveform is sampled. I have found that because of baseline fluctuations and other variables, the expected magnitude or value of the cardiac waveform and the probability that a particular value will recur cannot be known a priori. However, taking the difference between sampled values in two different measurement cycles does produce a value whose probability can be predicted. It is possible, therefore, to assign a digital code to each expected difference value such that difference values with a high expected probability have a shorter code and values with low probability have a longer code. The variability in code length or size permits the resulting digital representation of the waveform to be compressed. Furthermore, because the conversion process is completed when the difference is determined and the digital code is assigned, the energy required for conversion will be reduced. My invention, therefore, comprises means for comparing at least two sampled values of cardiac waveforms and for determining a difference between the sampled waveforms. Further, means are provided for assigning a digital code based on the determined difference, the digital code being of predetermined variable size, the size of the code being proportional to the predicted probability of occurrence of a particular difference.

Cardiac waveforms can be broadly categorized into normal cardiac waveforms (including bradycardia), tachyarrhythmias, and fibrillation. Each of these broad categories display somewhat different characteristics. For each type, therefore, the probabilities for particular detected differences change. My invention, therefore, provides for different codes to be assigned to a detected difference depending on the type of waveform which is being detected.

My invention may be realized using either analog or digital circuitry or a combination thereof.

With the foregoing in mind it is an object of my invention to provide an implantable stimulator with a specialized analog to digital converter for producing compressed digital representations of cardiac waveforms.

It is another object of my invention to provide such an analog to digital converter which can be optimized for the type of cardiac waveform being detected.

Another object of my invention is to provide such an analog to digital converter which produces a compressed digital representation of a waveform without an intervening digital conversion. These an other objects and features of my invention will be apparent from the detailed description taken with reference to the accompanying drawings.

DETAILED DESCRIPTION OF THE PRESENTLY PREFERRED EMBODIMENTS

Figure 1:
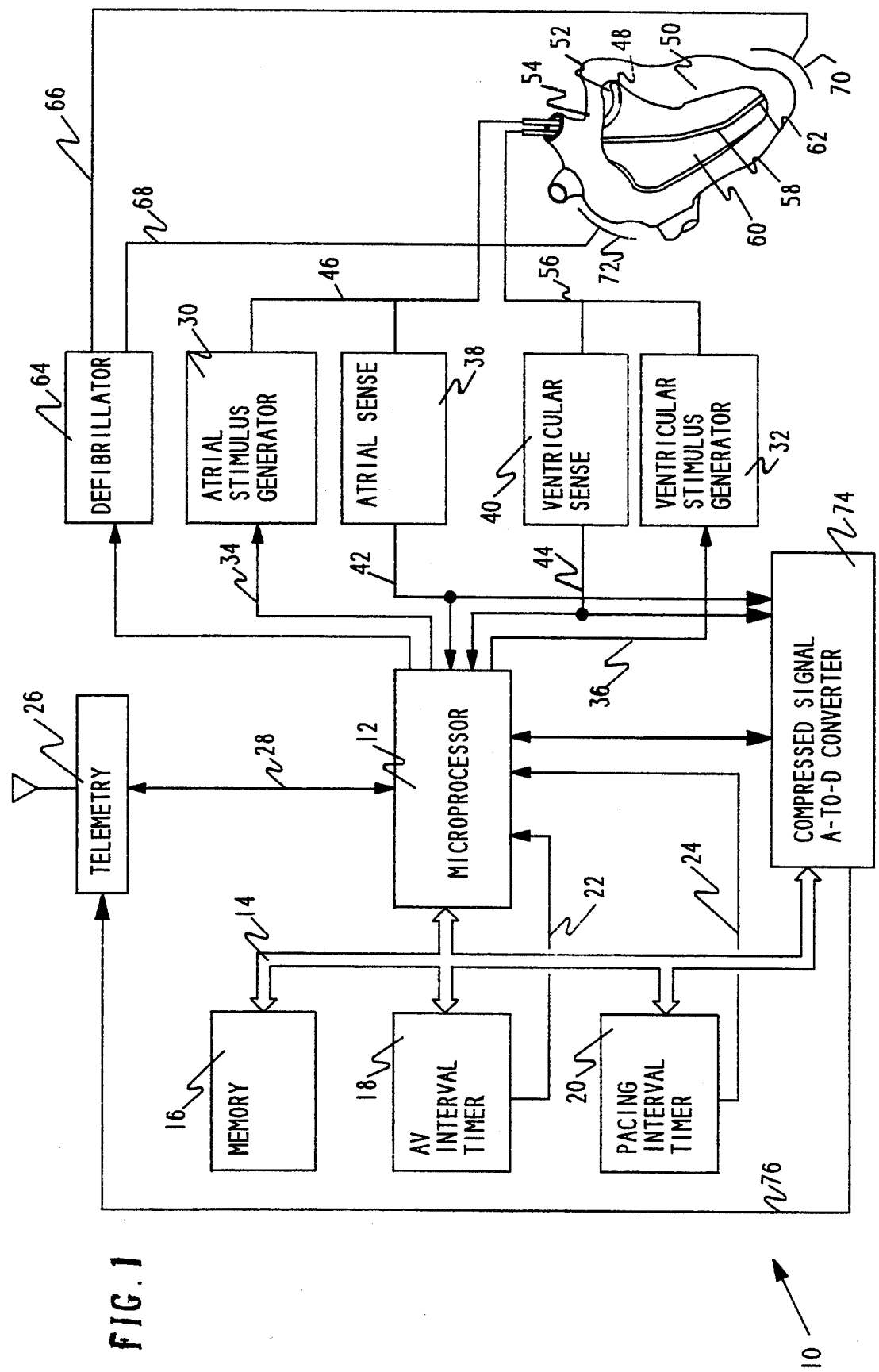
FIG. 1 is a block diagram of an implantable cardiac stimulator.

FIG. 1 is a block diagram illustrating an implantable cardiac stimulator 10 according to my invention. A microprocessor 12 preferably provides pacemaker control and computational facilities. It will be appreciated that other forms of circuitry, such as analog or discrete digital circuitry, can be used in place of microprocessor 12. However, a microprocessor is preferred for its miniature size and its flexibility, both of which are of critical importance in the implantable systems in which I believe my invention will be used. A particularly energy efficient microprocessor, which is designed specifically for use in pacemakers, is fully described in Gordon, et al., U.S. Pat. No. 4,404,972, which is assigned to the assignee of my invention.

The microprocessor 12 has input/output ports connected in a conventional manner via bidirectional bus 14 to memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively.

Memory 16 preferably includes both ROM and RAM. The microprocessor 12 may also contain additional ROM and RAM as described in Gordon, et al., U.S. Pat. No. 4,404,972. The pacemaker operating routine is stored in ROM. The RAM stores programmable parameters and variables in conjunction with the pacemaker operation.

The A-V and pacing interval timers 18 and 20 may be external to the microprocessor 12, as illustrated, or internal thereto, as described in the '972 patent. The timers 18 and 20 are suitable conventional up/down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22 and 24.

The microprocessor 12 preferably also has an input/output port connected to a telemetry interface 26 by line 28. The pacemaker, when implanted, is thus able to receive pacing and rate control parameters from an external programmer and to send data to an external receiver if desired. Many suitable telemetry systems are known to those skilled in the art. One such system and encoding arrangement is described in Calfee, et al., U.S. Pat. No. 4,539,992 which is also assigned to the assignee of my invention.

The microprocessor output ports are connected to inputs of an atrial stimulus pulse generator 30 and a ventricular stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines.

The microprocessor 12 also has input ports connected to outputs of an atrial sense amplifier 38 and a ventricular sense amplifier 40 by lines 42 and 44 respectively. The atrial and ventricular sense amplifiers 38, 40 detect occurrences of P-waves and R-waves respectively.

The input of the atrial sense amplifier 38 and the output of the atrial stimulus pulse generator 30 are connected to a first conductor 46 which is inserted in a first conventional lead 48. Lead 48 is inserted into a heart 50 intravenously or in any other suitable manner. The lead 46 has an electrically conductive pacing/sensing tip 52 at its distal end which is electrically connected to the conductor 46. The pacing/sensing tip 52 is preferably lodged in the right atrium 54.

The input of the ventricular sense amplifier 40 and the output of the ventricular stimulus pulse generator 32 are connected to a second conductor 56. The second conductor 56 is inserted in a second conventional lead 58 which is inserted intravenously or otherwise in the right ventricle 60 of the heart 50. The second lead 58 has an electrically conductive pacing/sensing tip 62 at its distal end. The pacing/sensing tip 62 is electrically connected to the conductor 56. The pacing/sensing tip 62 is preferably lodged on the wall of the right ventricle.

The conductors 30, and 32 conduct the stimulus pulses generated by the atrial and ventricular stimulus pulse generators 46,56, respectively, to the pacing/sensing tips 52, 62. The pacing/sensing tips 52, 62 and corresponding conductors 46, 56 also conduct sensed cardiac electrical signals in the right atrium and right ventricle to the atrial and ventricular sense amplifiers 38, 40.

In addition, it may be desired to provide defibrillation capability in the implantable device. If this is the case, a high voltage defibrillator circuit 64 is provided which is controlled by the microprocessor 12. The defibrillator circuit 64 is connected to heart tissue through two high voltage leads 66, 68 which communicate with the heart through electrodes 70, 72. In the illustrated embodiment, epicardial patch electrodes are diagrammatically represented. However, other electrode configurations, including endocardial electrodes, are known to those skilled in the art and may be used without departing from the spirit or teachings of my invention.

Those skilled in the art will recognize, from the further description of my invention, that my invention may be used with an implanted device which comprises only a defibrillator or only a single chamber pacer as well as a dual chamber pacer or any combination thereof and may in fact be used without stimulating the heart at all, if the sole intent is to record the cardiac waveform. It is necessary, however, to sense the cardiac waveform. This may be done remote from the heart or in either the atrium or the ventricle or both. In the illustrated embodiment, sensing occurs through the electrode tips 52, 62.

The atrial and ventricular sense amplifiers 38, 40 communicate both with the microprocessor and with a compressed signal A-to-D converter 74 which will be more fully described below. The compressed signal A-to-D converter 74 communicates through the bus 14 with memory 16 and the microprocessor 12, primarily, and on a line 76 with the telemetry 26. Thus, the output of the converter 74 can be manipulated by the microprocessor 12, or stored in memory 16 or directly communicated through the telemetry 26 to an external device (not shown). The stored output of the convertor 74 may also be subsequently communicated from memory 16 through the telemetry 26 to the external device.

Figure 5:
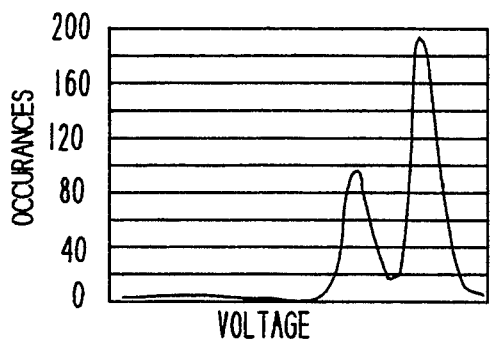
FIG. 5 is a graph representing occurrences of sampled electrical values in a heart.
Figure 6:
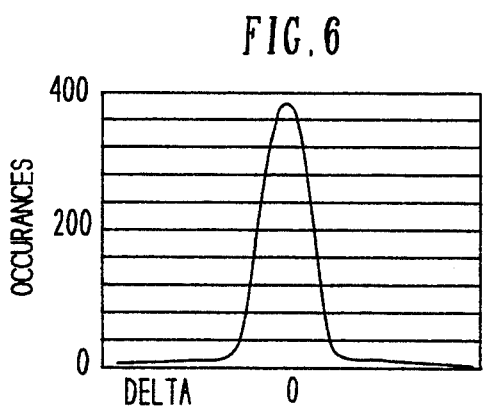
FIG. 6 is a graph representing occurrences of differences between successive samples of electrical values in the heart.

I have discovered that it possible to convert an analog cardiac electrogram signal to a digital representation in a compressed form without loss of information. The converter 74 compresses the data by assigning a digital output which is correlated to the probability of the occurrence of a particular feature of the analog signal. Due to preexisting charges in the heart and event variability, the probability of a particular absolute value of a cardiac signal cannot be predetermined. For example, FIG. 5 shows a histogram of the occurrences of particular magnitudes of a cardiac signal in sinus rhythm at regular intervals. In the example given, two peaks occur in the digital values. However, these values are quite variable due to, among other things, the factors mentioned above. On the other hand, the difference from one value to the next does present a more regular and predictable pattern. As shown in FIG. 6, by taking the delta value or difference between the current magnitude of the cardiac signal and the magnitude at a discrete time theretofore, a regular histogram can be obtained. This will always peak at 0 and shows an almost Gaussian distribution.

The A-to-D converter 74, therefore, accepts an analog input. At discrete time intervals the value of that input is measured by either analog or digital techniques. The difference between successive values of the input is determined and this delta value is represented by a preassigned code, the length of the digital code being proportional to the probability of the occurrence of a given delta value. Thus, delta values with a high probability of occurrence will have a short code, while delta values with a low probability of occurrence will have a longer code. The resulting digital data stream is compressed by up to 80% as compared to more standard techniques. The information originally represented by the analog signal can, therefore, either be stored in a smaller memory or transmitted in a shorter period of time in digital format. By incorporating this compression into the analog-to-digital conversion, the conversion process will be shortened and the power consumption will be less than A-to-D conversion followed by post-conversion compression.

Figure 2:
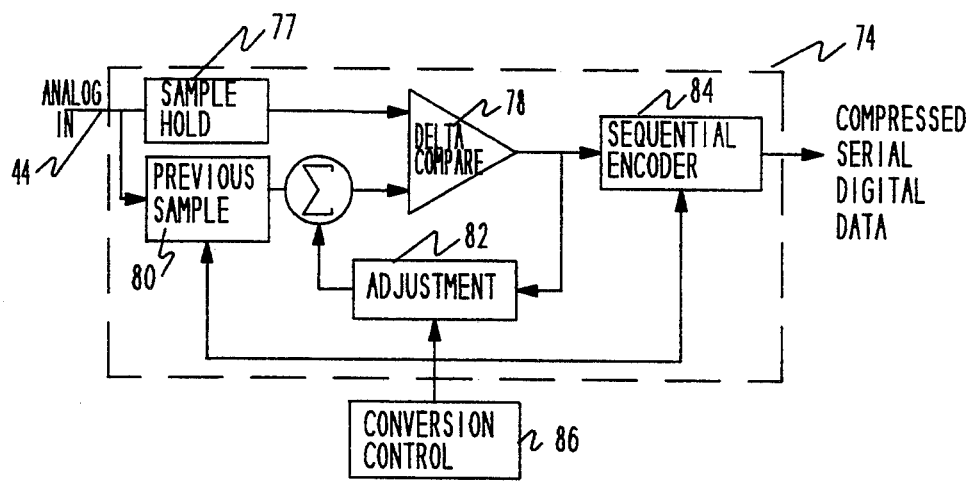
FIG. 2 is a block diagram of an analog-to-digital data converter.

Referring to FIG. 2, a conceptional representation of the A-to-D converter 74 according to my invention is illustrated. The converter 74 receives an analog cardiac signal along an input line, such as line 44. At the beginning of a measurement interval, the value of the analog signal is captured by a sample and hold circuit 77, This value is directed to a delta comparator 78. In addition, the signal is directed to a previous sample circuit 80 which stores the value of the signal from the previous measurement interval so that the output of the previous sample circuit 80 represents the value of the analog signal at some earlier time, off-set from the present time by a preselected interval, $\Delta T$. If there is difference between the two signals, as indicated by the output of the delta comparator, the magnitude of that difference is determined by operation of an adjustment circuit 82 in a feedback loop between the output of the comparator and at least one of the inputs, preferably the input from the previous sample circuit 80. The adjustment circuit 82 provides an additional signal to the input of the delta comparator until there is no difference between the two inputs. Thus, the difference between the two signals can be determined and this information can be communicated to a sequential encoder 84 which produces a digital signal representing the delta value, which digital signal has a length proportional to the probability of the occurrence of a particular delta value. In other words, values with high probability are represented by fewer bits than are values with low probability.

In the particular instance of cardiac signals, since the delta values are clustered around 0, the value of the conversion can be proportional to the length of time necessary to reduce the output of the delta comparator to 0. Thus, with a given cardiac signal input and a previous input from the previous sample circuit 80, the process of making incremental adjustments at fixed time intervals until the delta comparator produces a 0 value provides a time interval during which the conversion takes place and represents the desired information to the encoder 84. Because delta values which are away from 0 value have diminishing probability, an output from the sequential encoder can begin before the actual value of the difference or delta value has been completely determined.

Timing between the previous sample circuit 80, adjustment circuit 82 and sequential encoder 84 and other control signals are managed by conversion control circuits 86. The conversion control circuit 86 may be comprised of certain functions of the microprocessor mentioned above.

Figure 3:
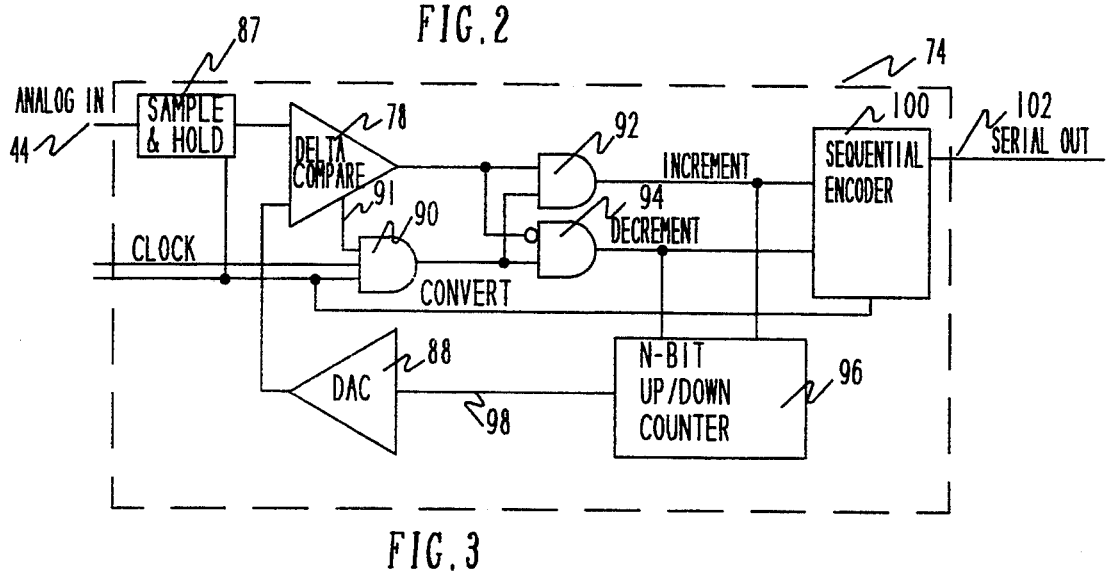
FIG. 3 is a digital embodiment of the analog-to-digital data converter.

I will now discuss a digital implementation of the converter 74 illustrated FIG. 3. As before, the converter is generally designated 74 and receives an analog input along a line such as the line 44 to a sample and hold circuit 87 and then to comparator 78. The comparator 78 is also receiving an analog signal from an N-bit digital-to-analog converter 88 which, as will be more completely explained hereafter, represents the value of the analog signal from the previous period. A three-input AND gate 90 gives a positive output if three conditions are met: the inputs to the delta comparator are not equal (signaled on line 91); there is a clock pulse present, and there is a convert signal present. The clock and the convert signals represent the conversion control 86 mentioned above. The output of the delta comparator and the AND gate 90 are led to two-input AND gates 92 and 94. One of the gates, specifically AND gate 94, has an inverted input between the comparator 78 and the gate 94. If the input from line 44 is greater than the signal from the digital-to-analog converter 88, the output of the AND gate 92 will indicate that N-bit up/down counter 96 should be incremented. On the other hand, if the analog signal on line 44 is less than the signal from the digital-to-analog converter 88, the output of the AND gate 94 will indicate that N-bit up/down converter should be decremented. Because the up/down converter 96 is already set to the previous value of the analog signal, incrementing or decrementing will bring the counter 96 to a digital representation of the actual value of the analog signal at a particular time. That value can then be transferred on an N-conductor line 98 to the digital-to-analog converter 88 for the next conversion. At the same time, the number of increment and decrement signals from the AND gates 92 and 94 within a particular conversion inform a sequential encoder 100 of the delta value. The sequential encoder 100 can then assign a digital representation of the delta value for output on a serial line 102. When the inputs to the comparator 78 are equal, an inputs-not-equal signal on line 91 will turn off the output of AND gate 90, thereby inhibiting increment and decrement signals until a subsequent conversion period when line 44 is not equal to the signal from the digital-to-analog converter 88.

Figure 8:
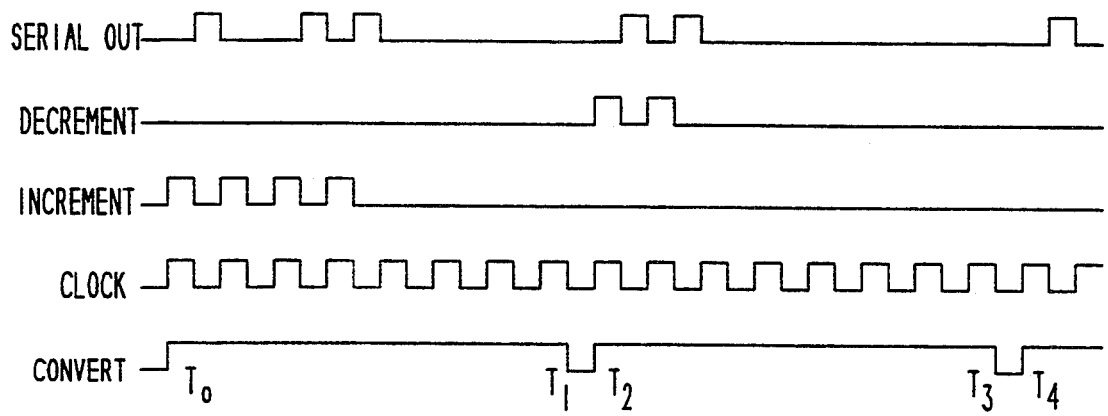
FIG. 8 is a timing diagram.

The operation of the converter 74 can be further understood by reference to FIG. 8 which illustrates a timing diagram. On the line labeled CONVERT in FIG. 3, a signal appears illustrated by the CONVERT signal shown in FIG. 8. A measurement interval is defined by a time interval such as $T_0$ to $T_1$ and $T_2$ to $T_3$. So long as the CONVERT signal is high, a measurement interval can take place. At the same time, a CLOCK signal appears on the CLOCK line as shown in FIG. 3. As illustrated in FIG. 8, the CLOCK signal comprises a series of equally spaced pulses. The number of pulses in any measurement interval will be related to the capacity of the N-bit up/down counter 96. If N is 8, for example, 256 pulses (or $2^n$), should generally occur in any measurement interval. In FIG. 8 I have only illustrated 8 pulses (or in $2^3$) in order to simplify the drawing. If the analog signal is rising during the first measurement cycle $T_0$–$T_1$, such that the signal on line 44 is higher than the signal during the previous cardiac measurement cycle, the INCREMENT line will go high during each clock pulse until the output of the digital-to-analog converter 88 equals the current input. A code representative of the magnitude of the incremental change will be transmitted on the serial out line 102. The sample and hold circuit 77 and previous sample 80 in FIG. 2 take instantaneous samples of the analog input signal. This output signal can start before the pulse stream on the INCREMENT line has stopped because, in any measurement interval, the output will be either monotonically incrementing or decrementing in any particular cycle. In the second cycle $T_2$-$T_3$ shown in FIG. 8, it is assumed that the analog input is lower in this cycle than in the previous cycle $T_0$-$T_1$. Thus, there will be decrement pulses appearing on the decrement line in FIG. 3 and transmitted to the sequential encoder 100. On the serial out line 102, another code will appear. Finally, if there is no difference between cycles, as suggested in the cycle starting $T_4$, there will be no signal on either the decrement or increment line. The absence of a high on either the decrement or increment line in the first clock cycle during a measurement cycle indicates that there has been no change and the sequential encoder 100 can transmit an appropriate code immediately. Since no change is the most expected condition, a single pulse, as shown in FIG. 8, is the most appropriate associated code. Each code should be uniquely associated with a particular difference and should have conventional termination signals separating the codes. Further these types of codes are sometimes known as Huffman codes. See, for example, "The Dawn Age: Minimum Redundancy Coding", *The Data Compression Book*, Mark Nelson, M& T Publishing, 1991, pp. 29-39.

Although the pulses shown on the serial out line in FIG. 8 are illustrated as being of the same duration as the clock pulses, the timing of the codes on the serial outline 102 does not need to be related to the clock in such a manner. They could be longer or shorter depending on the use to which the signals are to be put, for example, immediate transmission or storage or further processing by the microprocessor.

Figure 4:
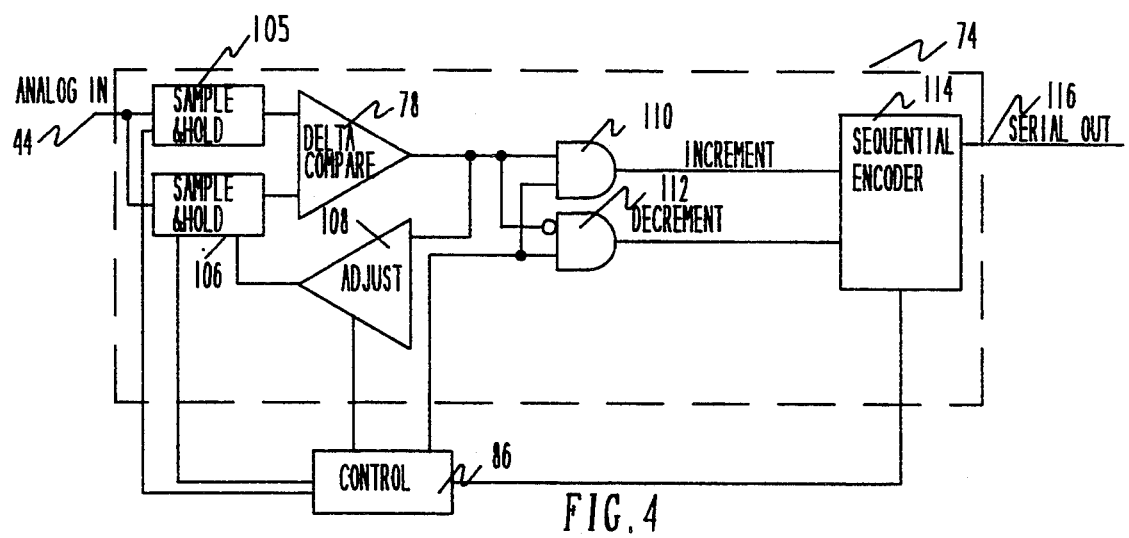
FIG. 4 is an analog embodiment of the analog-to-digital data converter.

FIG. 4 illustrates an analog implementation of the converter. As before, the converter is generally designated 74 and the analog input appears on line 44. The input is sampled at the beginning of a measurement interval by sample and hold circuit 105. A second sample and hold circuit 106 maintains the value of the analog signal from the previous time period, but the output of the sample and hold circuit 106 to the comparator 78 is adjusted by an analog amplifier 108. As in the digital implementation described above, the output of the comparator 78 is directed to AND gates 110 and 112. Like gate 94 above, gate 112 has an inverted input between the gate 112 and the comparator 78. Timing of the gates 110, 112, of the adjust amplifier 108 and of the sample and hold circuit 106 are controlled by the conversion control 86. Outputs from the AND gates 110 and 112 indicate to a sequential encoder 114 that the present analog signal is either above or below the previous signal. As in the previously described embodiments, the sequential encoder 114 assigns a code based on the delta value represented by the received increment or decrement signals within a particular time period and transmits that signal on a serial line 116.

Figure 7:
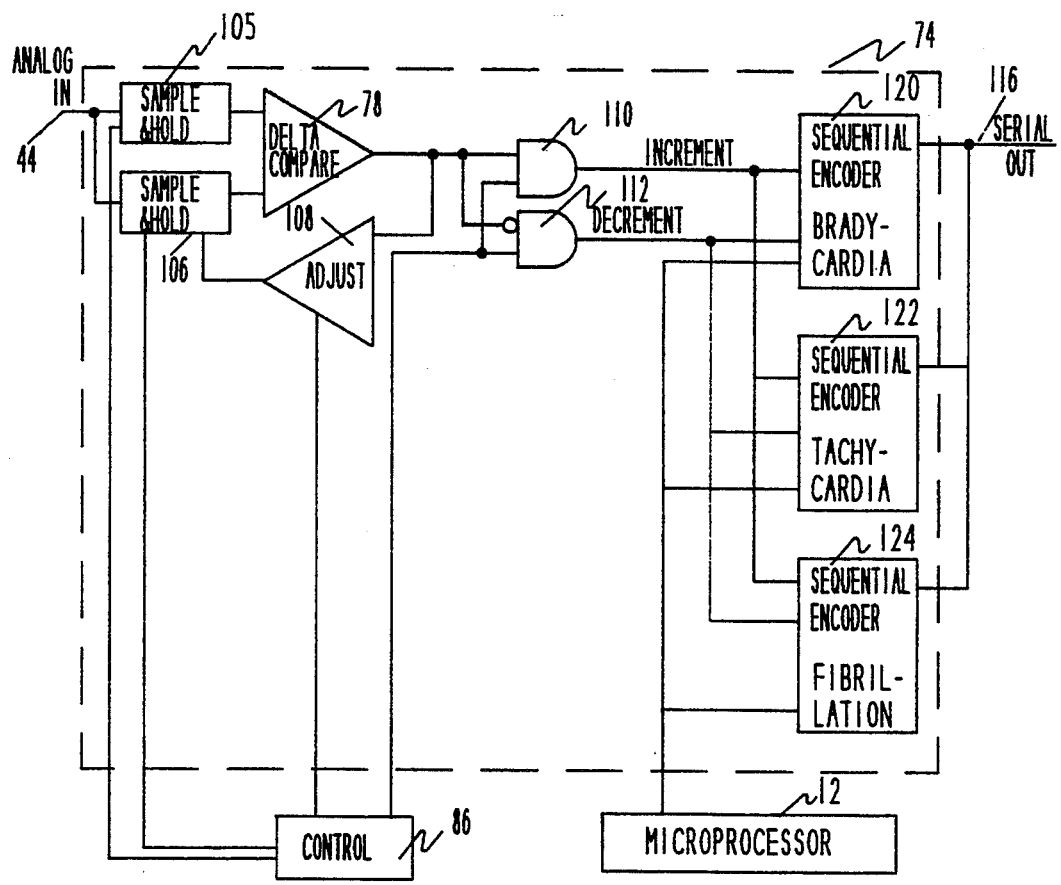
FIG. 7 is an analog embodiment with multiple encoders.

FIG. 7 illustrates a further elaboration of the converter illustrated in FIG. 4. It is known in the art that bradycardia signals, tachycardia signals and fibrillation signals in the heart have different characteristics, particularly with respect to frequency components and shape.

It is appropriate, therefore, to provide a different set of codes for a sequential encoder for each of these situations. Thus, a sequential encoder can be provided for each of these specialized instances, such as bradycardia encoder 120, tachycardia encoder 122 and fibrillation encoder 124. It is known in this art to distinguish between bradycardia, tachycardia and fibrillation by analysis of the electrical signals, frequently through the microprocessor 12. Upon recognition of any of these conditions, or others, the microprocessor 12 can control the encoders 120, 122 and 124 to select the appropriate encoder for the type of signal being detected.

My invention may be embodied in other specific forms without departing from the spirit and teachings thereof. The foregoing examples, therefore, are intended in all respects to be illustrative. The scope of my invention is defined by the appended claims, and all changes which come within the meaning of equivalency of the claims are intended to be encompassed therein.

I claim as my invention:

1. An implantable cardiac stimulator comprising:
   means for stimulating the heart;
   means for sensing intrinsic cardiac waveforms in the heart;
   means for converting said intrinsic cardiac waveforms from analog to digital form, said converting means consisting of
   timing means for defining measurement cycles;
   sampling means for sampling the analog value of said cardiac waveform in a measurement cycle;
   means for comparing at least two sampled analog values of said cardiac waveforms;
   means for determining an analog difference having a predicted probability of occurrence between said two sampled cardiac waveforms;
   means for assigning a digital code to said analog difference, said digital code being of predetermined, variable size, said size being proportional to the predicted probability of occurrence of said difference.

2. The cardiac stimulator according to claim 1 wherein the means for stimulating the heart comprise a pacemaker.

3. The cardiac stimulator according to claim 1 wherein the means for stimulating the heart comprise a defibrillator.

4. The cardiac stimulator according to claim 1 wherein said sampling means comprise
   a first sample and hold circuit for sampling the value of said cardiac waveform during the current cycle, and
   a second sample and hold circuit for storing the value of said cardiac waveform from a previous cycle.

5. The cardiac stimulator according to claim 4 wherein said means for comparing comprises a comparator.

6. The cardiac stimulator according to claim 5 wherein said means for determining a difference comprise an analog feed back from an output of said comparator to one of the sample and hold circuits.

7. The cardiac stimulator according to claim 6 wherein said means for determining a difference further comprises a first time-controlled gate in electrical contact with the output of said comparator for detecting a positive output from said comparator and a second time-controlled gate in electrical contact with the output of said comparator for detecting a negative output from said comparator.

8. The cardiac stimulator according to claim 1 wherein means for comparing comprise a comparator and said sampling means comprise a sample and hold circuit for sampling the value of said cardiac waveform during the current cycle, said sample and hold circuit being connected to an input of said comparator.

9. The cardiac stimulator according to claim 8 wherein said means for determining a difference further comprises a first time-controlled gate in electrical contact with the output of said comparator for detecting a positive output from said comparator and a second time-controlled gate in electrical contact with the output of said comparator for detecting a negative output from said comparator.

10. The cardiac stimulator according to claim 9 wherein said means for determining a difference further comprises an up-down counter having at least one input electrically connected to the output of said gates and an output connected to a second input of said comparator.

11. The cardiac stimulator according to claim 10 wherein said means for determining further comprises a digital-to-analog converter between said output of said up-down counter and said second input of said comparator.

12. The cardiac stimulator according to claim 11 wherein said means for assigning comprise a plurality of encoders, each encoder assigning codes for pre-selected categories of cardiac waveforms and means for selectively operating at least one of said encoders in response to detected characteristics of said cardiac waveform.

13. An analog-to-digital converter for cardiac waveforms comprising:
means for sensing intrinsic cardiac waveforms in the heart;
means for converting said intrinsic cardiac waveforms from analog to digital form, said converting means consisting of
  timing means for defining measurement cycles;
  sampling means for sampling the analog value of said cardiac waveform in a measurement cycle;
  means for comparing at least two sampled analog values of said cardiac waveforms;
  means for determining an analog difference between said two sampled cardiac waveforms;
  means for assigning a digital code to said analog difference, said digital code being of predetermined, variable size, said size being proportional to the predicted probability of occurrence of said difference.

14. The analog-to-digital converter according to claim 13 wherein said sampling means comprise
a first sample and hold circuit for sampling the value of said cardiac waveform during the current cycle, and
a second sample and hold circuit for storing the value of said cardiac waveform from a previous cycle.

15. The analog-to-digital converter according to claim 14 wherein said means for comparing comprises a comparator.

16. The analog-to-digital converter according to claim 15 wherein said means for determining a difference comprise an analog feed back from an output of said comparator to one of the sample and hold circuits.

17. The analog-to-digital converter according to claim 16 wherein said means for determining a difference further comprises a first time-controlled gate in electrical contact with the output of said comparator for detecting a positive output from said comparator and a second time-controlled gate in electrical contact with the output of said comparator for detecting a negative output from said comparator.

18. The analog-to-digital converter according to claim 13 wherein means for comparing comprise a comparator and said sampling means comprise a sample and hold circuit for sampling the value of said cardiac waveform during the current cycle, said sample and hold circuit being connected to an input of said comparator.

19. The analog-to-digital converter according to claim 18 wherein said means for determining a difference further comprises a first time-controlled gate in electrical contact with the output of said comparator for detecting a positive output from said comparator and a second time-controlled gate in electrical contact with the output of said comparator for detecting a negative output from said comparator.

20. The analog-to-digital converter according to claim 19 wherein said means for determining a difference further comprises an up-down counter having at least one input electrically connected to the output of said gates and an output connected to a second input of said comparator.

21. The analog-to-digital converter according to claim 20 wherein said means for determining further comprises a digital-to-analog converter between said output of said up-down counter and said second input of said comparator.

22. The analog-to-digital converter according to claim 21 wherein said means for assigning comprise a plurality of encoders, each encoder assigning codes for pre-selected categories of cardiac waveforms and means for selectively operating at least one of said encoders in response to detected characteristics of said cardiac waveform.

* * * * *